United States Patent
Schumacher et al.

(10) Patent No.: US 8,087,329 B2
(45) Date of Patent: Jan. 3, 2012

(54) SCREWDRIVER FOR BONE SCREWS

(75) Inventors: Joerg Schumacher, Tuttlingen (DE); Ulrich Kramer, Oberwangen (CH)

(73) Assignee: Aesculap AG, Tuttlingen (DE)

( * ) Notice: Subject to any disclaimer, the term of this patent is extended or adjusted under 35 U.S.C. 154(b) by 869 days.

(21) Appl. No.: 12/070,337

(22) Filed: Feb. 15, 2008

(65) Prior Publication Data

US 2008/0215061 A1  Sep. 4, 2008

Related U.S. Application Data

(63) Continuation of application No. PCT/EP2006/006423, filed on Jul. 1, 2006.

(30) Foreign Application Priority Data

Sep. 9, 2005  (DE) .......................... 10 2005 044 445
Dec. 9, 2005  (DE) .......................... 10 2005 058 868

(51) Int. Cl.
B25B 23/081 (2006.01)

(52) U.S. Cl. ................ 81/454; 81/451; 81/452; 81/453; 81/455; 606/104

(58) Field of Classification Search .................. 606/104, 606/279; 81/125, 451–455
See application file for complete search history.

(56) References Cited

U.S. PATENT DOCUMENTS

| | | | |
|---|---|---|---|
| 2,701,494 A | 2/1955 | Johnson | |
| 3,245,446 A * | 4/1966 | Morifuji | 81/452 |
| 3,604,487 A * | 9/1971 | Gilbert | 81/443 |
| 4,060,114 A * | 11/1977 | Matsushima | 81/448 |
| 4,399,898 A * | 8/1983 | Olschewski et al. | 192/98 |
| 4,763,548 A | 8/1988 | Leibinger et al. | |
| 5,237,893 A * | 8/1993 | Ryder et al. | 81/452 |
| 5,667,513 A * | 9/1997 | Torrie et al. | 606/104 |
| 6,415,693 B1 | 7/2002 | Simon et al. | |
| 2002/0020255 A1 | 2/2002 | Simon et al. | |
| 2005/0092142 A1 | 5/2005 | Nish | |
| 2006/0200132 A1 * | 9/2006 | Chao et al. | 606/61 |

FOREIGN PATENT DOCUMENTS

| | | |
|---|---|---|
| DE | 35 39 502 | 2/1987 |
| DE | 200 13 905 | 1/2001 |
| DE | 100 42 424 | 3/2002 |
| DE | 10042424 | * 3/2002 |
| WO | WO03086713 | * 10/2003 |

* cited by examiner

*Primary Examiner* — Nicholas Woodall
*Assistant Examiner* — Samuel Hanna
(74) *Attorney, Agent, or Firm* — Lipsitz & McAllister, LLC

(57) ABSTRACT

In a screwdriver for bone screws, having a handle and rotationally fixedly held thereon a shaft, the free end of which has a non-circular cross section and is insertable in a positively locked manner in a non-circular receiving opening in the head of a bone screw, at least one expander element being mounted so as to be displaceable in the longitudinal direction in the shaft and so as to slide, when displaced in the longitudinal direction, along a slide surface in the area of the free end of the shaft in such a way that it projects laterally over the contour of the shaft, in order to simplify the actuation of the at least one expander element, it is proposed that the at least one expander element be pretensioned by an elastic spring element in the direction towards the free end of the shaft and be retractable against the action of the spring element in the shaft until it no longer projects laterally over the contour of the shaft.

19 Claims, 7 Drawing Sheets

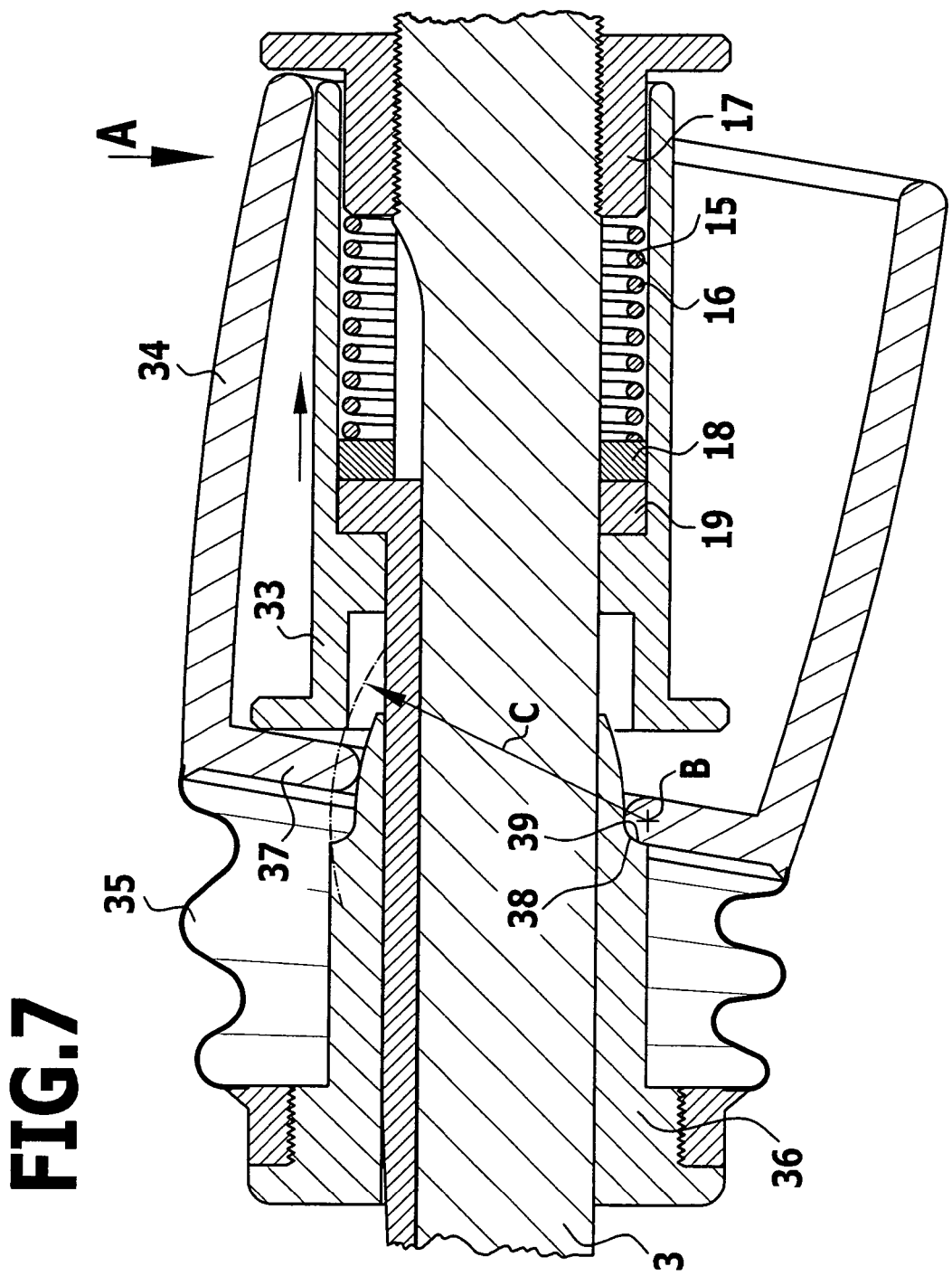

SCREWDRIVER FOR BONE SCREWS

This application is a continuation of international application number PCT/EP2006/006423 filed on Jul. 1, 2006.

The present disclosure relates to the subject matter disclosed in international application number PCT/EP2006/006423 of Jul. 1, 2006 and German applications number 10 2005 044 445.8 of Sep. 9, 2005 and number 10 2005 058 868.9 of Dec. 9, 2005, which are incorporated herein by reference in their entirety and for all purposes.

BACKGROUND OF THE INVENTION

The invention relates to a screwdriver for bone screws, having a handle and rotationally fixedly held thereon a shaft, the free end of which has a non-circular cross section and is insertable in a positively locked manner in a non-circular receiving opening in the head of a bone screw, at least one expander element being mounted so as to be displaceable in the longitudinal direction in the shaft and so as to slide, when displaced in the longitudinal direction, along a slide surface in the area of the free end of the shaft in such a way that it projects laterally over the contour of the shaft.

Such a screwdriver is described in DE 100 42 424 C2. With this screwdriver, the shaft can be releasably connected to the bone screw in a simple way by advancing the expander element, so that the bone screw is held at the free end of the shaft and can be taken to the intended point of application.

In the known screwdriver, the expander element is advanced by means of a sleeve which is rotatably mounted on a thread of the shaft. The object of the invention is to so construct a generic screwdriver that the advancing and retracting of the expander element are simpler than with the known screwdriver.

SUMMARY OF THE INVENTION

This object is accomplished in a screwdriver of the kind described at the outset, in accordance with the invention, in that the at least one expander element is pretensioned by an elastic spring element in the direction towards the free end of the shaft and is retractable against the action of the spring element in the shaft until it no longer projects laterally over the contour of the shaft.

By using such a spring element, the at least one expander element, i.e., one, two or more expander elements, is automatically moved into the advanced clamping position in which the shaft is pressed in a forceful and positively locked manner by the at least one expander element against the inside wall of the receiving opening of the bone screw. A connection between screwdriver and bone screw is thereby effected automatically. To release this connection, the at least one expander element need only be retracted against the action of the elastic spring element. The operator can, therefore, release the connection in a simple way and also reestablish it in just as simple a way by releasing the elastic spring element, which then automatically displaces the at least one expander element into the advanced clamping position.

It is favorable for a stop to be provided for limiting the advancing movement of the at least one expander element in the direction towards the free end of the shaft, so that the advancing movement of the at least one expander element is limited when the shaft does not engage the receiving opening of a bone screw.

Provision is made in accordance with a preferred embodiment for the at least one expander element to be connected via a transmission member to an advancing device located on the handle, and for the spring element to be part of the advancing device. In this way, the operator can retract or release the expander element, i.e., release or secure the connection between bone screw and screwdriver, in the area of the handle.

It is favorable for the transmission member to comprise at least one bar which is placed in at least one longitudinal groove which is laterally open and extends over the entire shaft as far as the handle. One, two or more bars may be provided, and, similarly, one, two or more longitudinal grooves.

In accordance with a preferred embodiment, the advancing device comprises a sleeve which is connected to the at least one expander element and is displaceable on the shaft. The at least one expander element can thus be retracted into the release position by displacement of the sleeve on the shaft.

To facilitate the retraction, it is favorable for the sleeve to carry gripping surfaces which project laterally. In particular, these may be formed by a radially projecting ring flange.

In a modified embodiment, a swivel element which is mounted on the shaft for swivel movement at one end and is able to swivel about this bearing point against the shaft is provided for displacing the sleeve. The swivel element comprises a driver which displaces the sleeve against the action of the spring element when the swivel element is swiveled against the shaft. The user can thus displace the sleeve and, consequently, retract the expander element by actuating this swivel element.

This swivel element can be configured as a simple swivel lever, however, a configuration is particularly advantageous, in which the swivel element is configured as a swivel sleeve surrounding the sleeve. Such a swivel sleeve surrounds the sleeve at all sides and can be swiveled in any direction against the shaft, so that the user can perform this swiveling independently of the angular position of the screwdriver.

It is favorable for the swivel element to be held by an elastically deformable holder on the shaft, and for the bearing point to be formed by a supporting element of the swivel element on the shaft. The bearing point is thus formed solely by the abutment of the supporting element on the shaft or on a part fixedly connected thereto. A fixing of the swivel sleeve on the shaft or on a part connected thereto is, however, effected by means of the elastically deformable holder.

This can be advantageously formed by a bellows concentrically surrounding the shaft.

In a preferred embodiment, the supporting element is formed by a ring flange projecting inwardly on the inner side of the swivel sleeve. In accordance with a particularly preferred embodiment, this can also simultaneously form the driver, which displaces the sleeve and, consequently, the expander element on the shaft when the swivel sleeve is swiveled.

If suitably configured, the resetting force of the bellows upon swiveling the swivel sleeve may be so strong that this bellows alone forms the elastic spring element which pretensions the expander element in the position of rest in the direction towards the free end of the shaft.

It is particularly advantageous for the sleeve to surround the shaft in spaced relation thereto, and for a helical spring which surrounds the shaft and is supported on the shaft and on the at least one expander element to be arranged as spring element in a ring space between sleeve and shaft. A very space-saving and compact assembly is then obtained for retracting and automatically clamping the at least one expander element.

In accordance with a particularly preferred embodiment, provision is made for the at least one longitudinal groove and the at least one bar to be of such dimensions that, at least in the area of the free end of the shaft, the at least one bar engages the at least one longitudinal groove without play. It is thereby ensured that in the area in which the shaft abuts on the inside wall of the receiving opening in the bone screw no free spaces for the shaft remain, into which the material of the shaft could flow when subjected to mechanical stress. The deformation of the shaft caused by such a flow is thereby definitely avoided.

In a preferred embodiment, for example, the at least one longitudinal groove and the at least one bar have, at least in the area of the free end of the shaft, planar side surfaces having the same inclination and converging towards the bottom of the groove. The at least one bar then abuts with these inclined side surfaces on the identically inclined side surfaces of the at least one longitudinal groove with surface-to-surface contact, so that freedom from play is thereby achieved. The side surfaces of the at least one longitudinal groove may simultaneously serve as slide surface, for example, by the spacing of the side surfaces of the at least one longitudinal groove from one another decreasing in size towards the free end of the shaft or by the at least one longitudinal groove extending to a lesser depth into the shaft towards the free end.

The at least one bar is preferably, at least in the area of the free end of the shaft, wider on its underside facing the bottom of the groove than the bottom of the groove, so that a spacing remains between the underside and the bottom of the groove when inserting the at least one bar into the at least one longitudinal groove. It is thereby ensured that the at least one bar will always abut via the converging side surfaces on the corresponding side surfaces of the at least one longitudinal groove.

It may be provided that the side walls of the at least one longitudinal groove continue, at least in the area of the free end of the shaft, via a rounding-off into the bottom of the groove. The stability of the shaft is thereby increased, as sharp edges are avoided in the area of transition between the side surfaces and the bottom of the groove.

The bottom of the groove may have, at least in the area of the free end of the shaft, an arcuate cross section.

It also advantageous for the side walls of the at least one bar to also continue, at least in the area of the free end of the shaft, via a rounding-off into the underside. The underside of the at least one bar may also have, at least in the area of the free end of the shaft, an arcuate cross section.

The shaft with its non-circular cross section is pressed by the at least one expander element against the inside wall of the receiving opening, whereby a rotational locking is enabled by the non-circular cross sections of shaft and receiving opening and the positive locking between these surfaces. In principal, such a rotational locking could be achieved by, for example, a regular hexagonal shape for the receiving opening and the shaft. However, with such a shaping, the shaft is pressed by the at least one expander element with only one surface of the hexagonal cross section against only one surface of the hexagonal receiving opening. A better torque transmission would be achieved if the abutment occurred at several surfaces. To achieve this, provision is made, in accordance with a preferred embodiment of the invention, for the non-circular cross section of the receiving opening and the non-circular cross section of the free end of the shaft to be configured such that the shaft is pressed by the at least one expander element in two areas of the receiving opening that are separate from one another against an inside wall of the receiving opening. A contact between the shaft and the receiving opening is then obtained at three locations in the circumferential area, namely, on the one hand, in the area of the at least one expander element, and, on the other hand, in the area of the two areas of the receiving opening that are separate from one another, with the result that an enlarged transmission surface area is made available for the torque.

In particular, provision may be made for the receiving opening to have the shape of a regular symmetrical hexagon or octagon, and for the shaft to be of substantially complementary shape, the side surface of the shaft that lies opposite the at least one expander element being set back radially inwardly to a slight extent. The cross section of the shaft is, therefore, not exactly symmetrical, but deviates slightly from the symmetry. It is thereby ensured that the two side surfaces adjoining the side surface of the shaft that lies opposite the at least one expander element will, in any case, abut on corresponding inner surfaces of the receiving opening. Consequently, the torque transmission occurs not only at the surface that lies opposite the at least one expander element, but at the two surfaces adjacent to this surface and at the at least one expander element.

The advantageous embodiments of the screwdriver described herein, which relate, in particular, to the mounting of the bar without play in the at least one longitudinal groove and/or to the abutment of the shaft on the inside wall of the receiving opening in areas that are separate from one another, are particularly advantageous in combination with the spring-loaded actuation of the at least one expander element. However, these features may also be employed in screwdrivers in which the at least one expander element is not displaced in the described manner by an elastic spring element into the clamping position, i.e., for example, in a screwdriver such as that described in DE 100 42 424 C2. The mounting of the bar without play in the longitudinal groove and the abutment of the shaft on separate areas of the receiving opening are particularly favorable in combination, but each of these features may also be realized on its own on a screwdriver. Such embodiments are also intended to be covered by the scope of the present invention.

The following description of preferred embodiments of the invention serves in conjunction with the drawings for further explanation.

BRIEF DESCRIPTION OF THE DRAWINGS

FIG. 7 shows a sectional view of the advancing device of FIG. 6 taken along line 7-7 with a tensioned spring element.

DETAILED DESCRIPTION OF THE INVENTION

Figure 1:
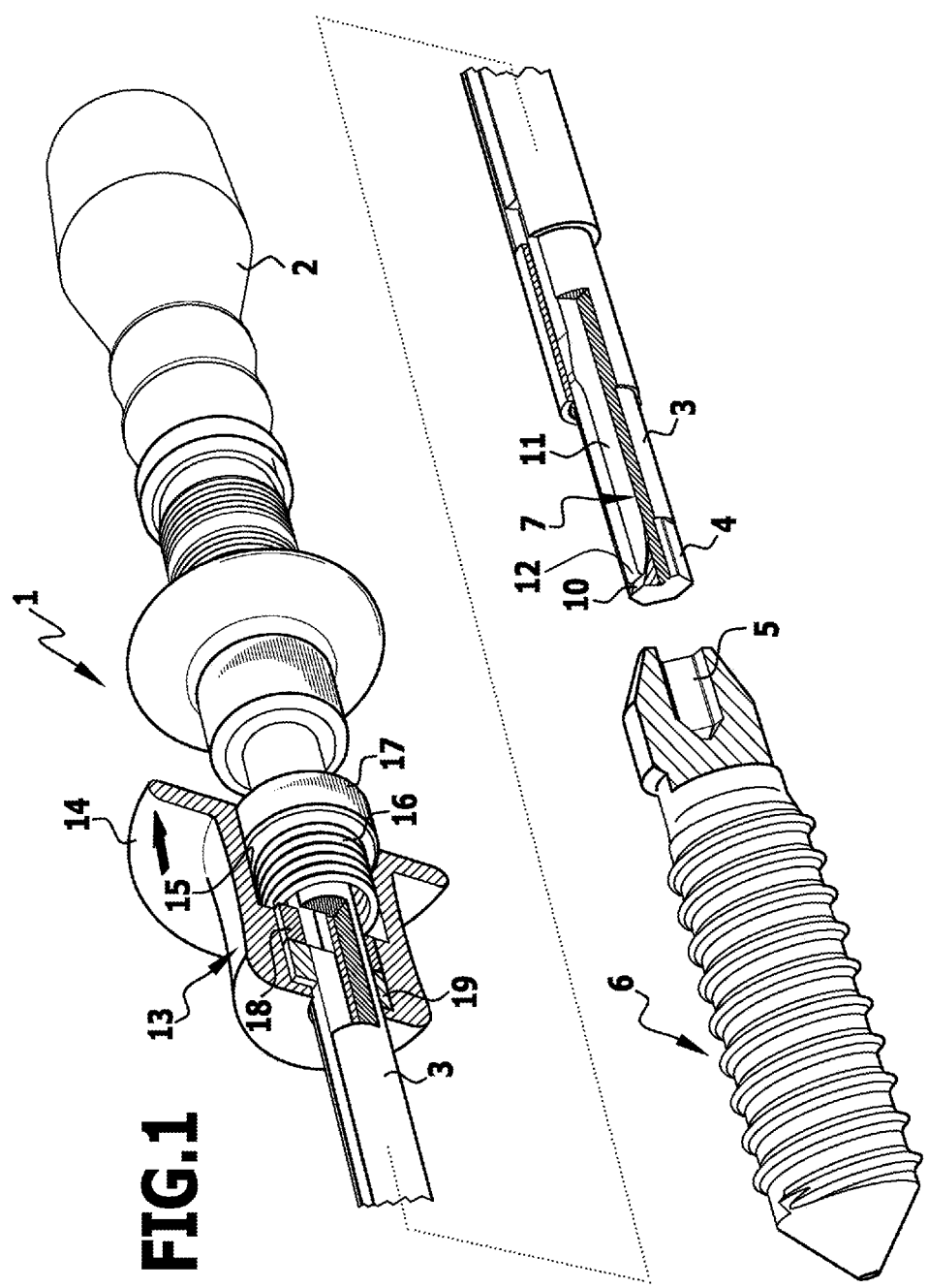
FIG. 1 shows a perspective view of a screwdriver with a spring-loaded expander element and a bone screw prior to insertion of the shaft of the screwdriver into a receiving opening of the bone screw.

The screwdriver 1 shown in the drawings comprises a handle 2 and rotationally fixedly held thereon a shaft 3, which is of hexagonal cross section (FIG. 3) at its free end 4.

This free end 4 can be inserted, in a manner known per se, into a receiving opening 5 of substantially complementary construction of a bone screw 6, so that a rotationally fixed, positively locked connection is made in this area between shaft 3 and bone screw 6. Arranged in the shaft 3 and extending over the major part of its length is a longitudinal groove 7 which is open towards the side surface. The width of the longitudinal groove 7 is less than the spacing between two adjacent edges 8 of the hexagonal cross section at the free end 4 of the shaft 3, the longitudinal groove 7 being located exactly in the middle between two adjacent edges 8. The depth of the longitudinal groove 7 is somewhat less than half of the diameter of the shaft 3. In the area of the free end 4, the bottom 9 of the longitudinal groove 7 continues into a slide surface 10 having the shape of an arc of a circle in longitudinal section, which tangentially adjoins the planar bottom 9 and rises up to the outer side of the shaft 3, so that the depth of the longitudinal groove 7 drops to zero (FIG. 2) at the free end 4 of the shaft 3.

Figure 2:
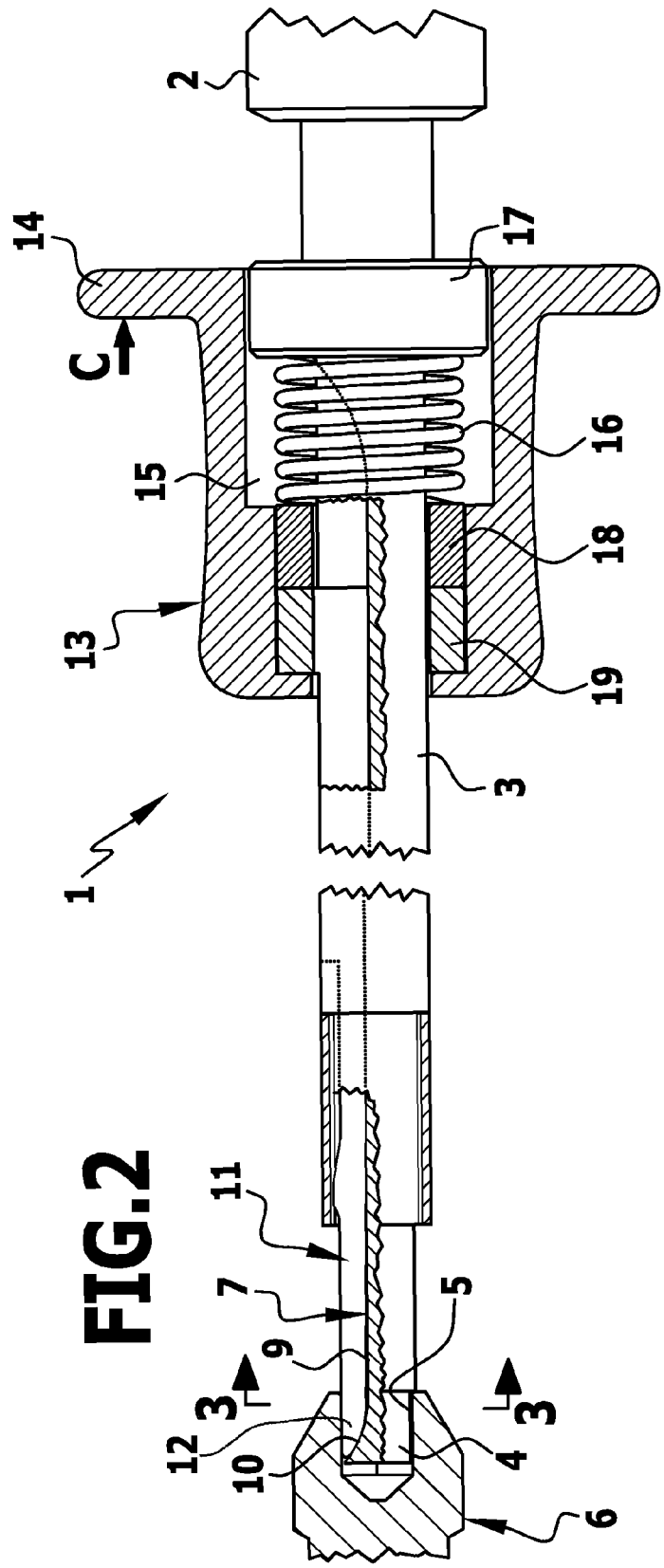
FIG. 2 shows a longitudinal sectional view of a portion of the screwdriver of FIG. 1 after insertion into the head of a bone screw.

On the side of the shaft 3 that is adjacent to the handle 2, the longitudinal groove 7 extends into the interior of the handle 2 (FIG. 2).

Mounted inside the longitudinal groove 7 is a bar 11, which is adapted to the contour of the longitudinal groove 7 and is guided in the longitudinal groove 7 so as to be freely displaceable in the longitudinal direction thereof. At its end 12 adjacent to the free end 4 of the shaft 3, the bar 11 is rounded-off in arcuate configuration, and this arcuate contour corresponds substantially to the arcuate contour of the slide surface 10. Aside from that, the bar 11 fills out the longitudinal groove substantially and extends in the longitudinal direction as far as almost the handle 2.

At the handle end of the longitudinal groove 7, the shaft 3 is surrounded by a grip sleeve 13, which is freely displaceable in the longitudinal direction on the shaft 3. At its end facing the handle 2, the grip sleeve has a radially projecting ring flange 14, which forms a ring-shaped gripping surface.

The grip sleeve 13 surrounds the shaft 3 in spaced relation thereto, thereby forming between the grip sleeve 13 and the shaft 3 a ring space 15, in which a helical spring 16 surrounding the shaft 3 is arranged. The helical spring 16 is supported, on the one hand, on a ring flange 17, fixedly connected to the shaft 3, and, on the other hand, via a ring 18, surrounding the shaft 3, to a ring-shaped widening 19 of the bar 11, similarly surrounding the shaft 3. At its handle end, the bar 11 is fixedly connected to this widening 19, so that the bar 11 is displaced by the helical spring 16 in the direction towards the free end 4 of the shaft 3.

The grip sleeve 13 engages around the widening 19 at the side thereof that faces away from the handle 2, so that upon displacing the grip sleeve 13 in the direction towards the handle 2 (i. e. in the direction of arrow C in FIG. 2), the bar 11 is displaced in the longitudinal groove 7 in the direction towards the handle 2, and the helical spring 16 is thereby elastically compressed. When the grip sleeve 13 is released again, the helical spring 16 relaxes and displaces the bar 11 in the direction towards the free end 4 of the shaft again. The dimensions are selected such that when the helical spring 16 is relaxed, the bar 11 is raised laterally out of the longitudinal groove 7 at the free end 4 and projects laterally over the contour of the shaft, whereas the bar 11 enters the longitudinal groove 7 fully at the free end 4 of the shaft 13 when the grip sleeve 13 is retracted in the direction towards the handle 2 and the helical spring 16 is thereby tensioned.

To insert the free end 4 of the shaft 3 into the receiving opening 5 of a bone screw 6, it is sufficient for the operator to displace the grip sleeve 13 in the direction of arrow C and thereby tension the helical spring 16. It is then readily possible to insert the free end of the shaft 3 into the receiving opening 5 as the bar 11 is fully accommodated in the longitudinal groove 7. Once the shaft 3 is inserted in the receiving opening 5, the operator can release the grip sleeve 13, as a result of which, under the action of the relaxing helical spring 16, the bar 11 (transmission member) is advanced in the direction towards the free end 4, so that the expander element (end 12 of the bar 11) is pressed by the slide surface 10 radially outwardly against the inside wall of the receiving opening 5, and the free end of the shaft 3 is thereby clamped in the receiving opening 5.

In this way, a clamped connection between screwdriver 1 and bone screw 6, with the shaft 3 abutting substantially with positive locking on the inside wall of the receiving opening 5, is obtained.

If the hexagonal cross section of the shaft 3 and the hexagonal cross section of the receiving opening 5 were exactly identical, an abutment with exact positive locking over the entire circumference between shaft and receiving opening would be obtained. However, this is not possible in practice, as manufacturing tolerances have to be taken into account. It is, therefore, necessary for the dimensions of the shaft 3 to be slightly less than the dimensions of the receiving opening. The necessary consequence of this is, however, that under the action of the outwardly tensioned end of the bar 11, the opposite surface of the shaft 3 is pressed against only one side surface of the receiving opening 5, and, an abutment is, therefore, only obtained on opposite sides of the receiving opening.

In order to also improve the abutment between shaft 3 and receiving opening 5 when slight play must be provided for compensation of manufacturing tolerances, it is advantageous to allow the cross section of the shaft 3 to deviate slightly from the shape of a regular hexagon. This is effected by the surface 20 of the shaft 3 that lies opposite the longitudinal groove 7 being slightly set back radially inwardly in relation to the surface of a regular hexagon. As a result, there is a slight spacing between this surface 20 and the directly opposite surface 21 of the receiving opening 5, and this results in the inclined surfaces 22 and 23 adjoining the surface 20 of the shaft 3 on either side thereof abutting with surface-to-surface contact on the identically inclined surfaces 24 and 25 of the receiving opening 5 that directly adjoin the surface 21 of the receiving opening 5. An abutment over a larger surface area between shaft 3 and receiving opening 5 is thereby obtained, the abutment occurring in three separate areas, namely in the area of the outwardly tensioned bar 11 and in the area of the lateral surfaces 22 and 23.

Figure 3:
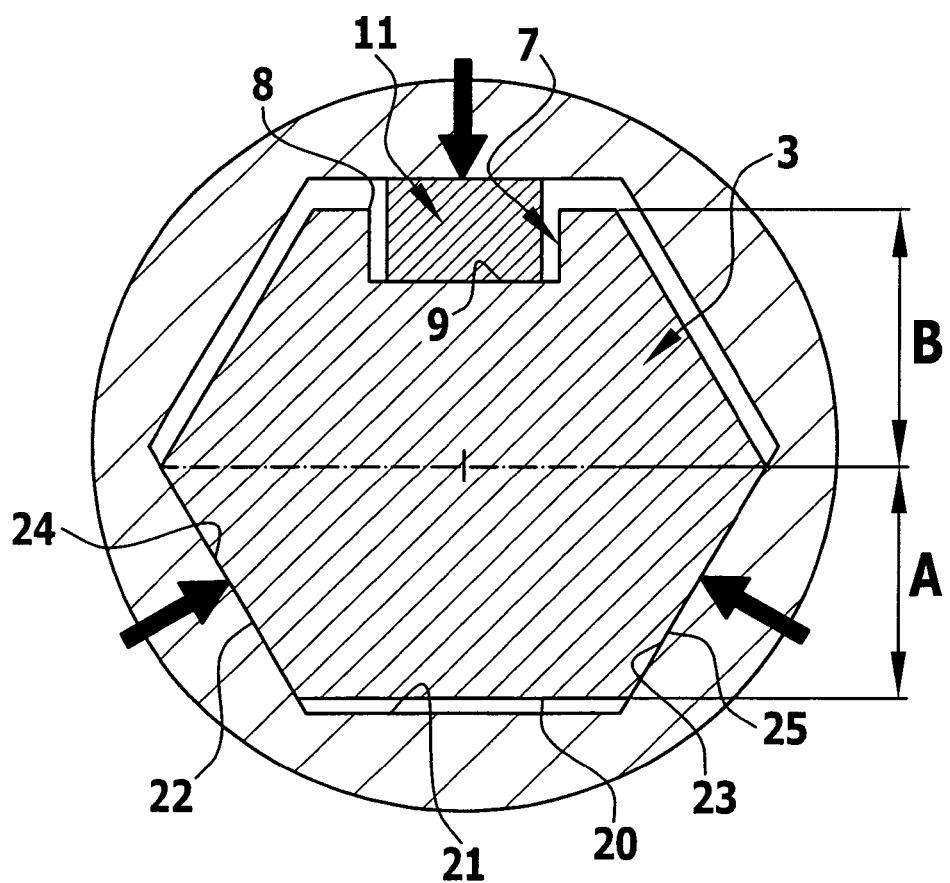
FIG. 3 shows a longitudinal sectional view taken along line 3-3 in FIG. 2 with a shaft of asymmetrical, hexagonal cross section.

Accordingly, in the embodiment shown in FIG. 3, the regular hexagonal cross section of the shaft 3 is modified such that the height A of the shaft on the side that lies opposite the longitudinal groove 7 is slightly less than the height B of the shaft on the side of the longitudinal groove 7. This difference may be very slight, for example, in the order of magnitude of a few tenths of a millimeter. For the purpose of clarification, this difference is shown exaggeratedly in FIG. 3.

A similar configuration is also possible when, for example, a regular octagon is chosen instead of a cross section of a regular hexagon.

In the embodiment of FIG. 3, the longitudinal groove 7 is rectangular in cross section, and the bar 11 also has a rectangular cross section. In order to also compensate manufacturing tolerances here, it is necessary for the bar 11 to be guided with play in the longitudinal groove 7. This play is shown exaggeratedly in FIG. 3. However, the consequence of this play is that during the transmission of large torques, the material of the shaft 3 can undergo a deformation into the space between the shaft 3 and the bar 11, i. e., the stability of the shaft 3 can suffer.

Figure 4:
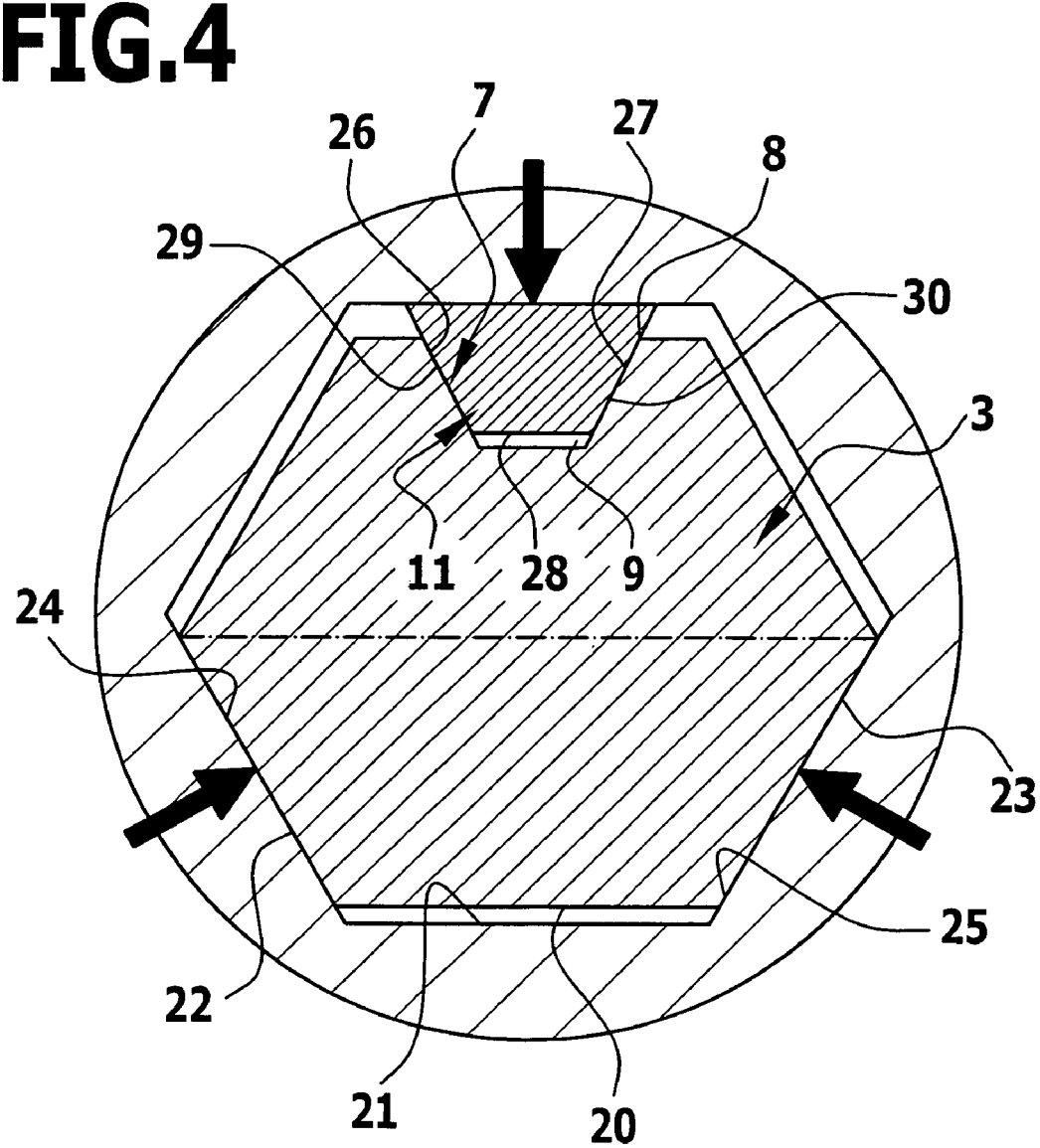
FIG. 4 shows a view similar to FIG. 3 with a longitudinal groove for the expander element having inclined, planar side walls.

With a view to avoiding this, a modified embodiment is shown in FIG. 4. In contrast to the configuration according to FIG. 3, the cross section of the longitudinal groove 7 and the bar 11 is altered in the embodiment according to FIG. 4. In this embodiment, the longitudinal groove 7 has a planar bottom 9 and two planar side surfaces 26 and 27 converging towards the bottom 9. The angle can be, for example, 30° in relation to the vertical. The bar 11 is also of planar configuration on its underside 28, and this planar underside 28 is adjoined on either side by planar side surfaces 29, 30 converging towards the underside 28. The width of the underside 28 is slightly larger than the width of the bottom 9 of the longitudinal groove 7, so that a small spacing remains between the underside 28 and the bottom 9. The side surfaces 29 and 30 abut with surface-to-surface contact on the side surfaces 26 and 27, so that the bar 11 is mounted without play in the longitudinal groove 7. A deformation of the shaft 3 is thereby prevented.

Provision may be made in this embodiment for the side surfaces 26 and 27 to form the slide surfaces that drive the bar radially outwardly when it is advanced. It is, therefore, not absolutely necessary for the bottom 9 to be shaped outwards, as shown in the embodiment of FIG. 2. If the spacing between the two side surfaces 26 and 27 becomes smaller towards the free end 4 of the shaft 3, the bar 11 is automatically pushed outwards when it is advanced in the longitudinal groove. The same applies when overall the longitudinal groove 7 has a lesser depth towards the free end 4.

Figure 5:
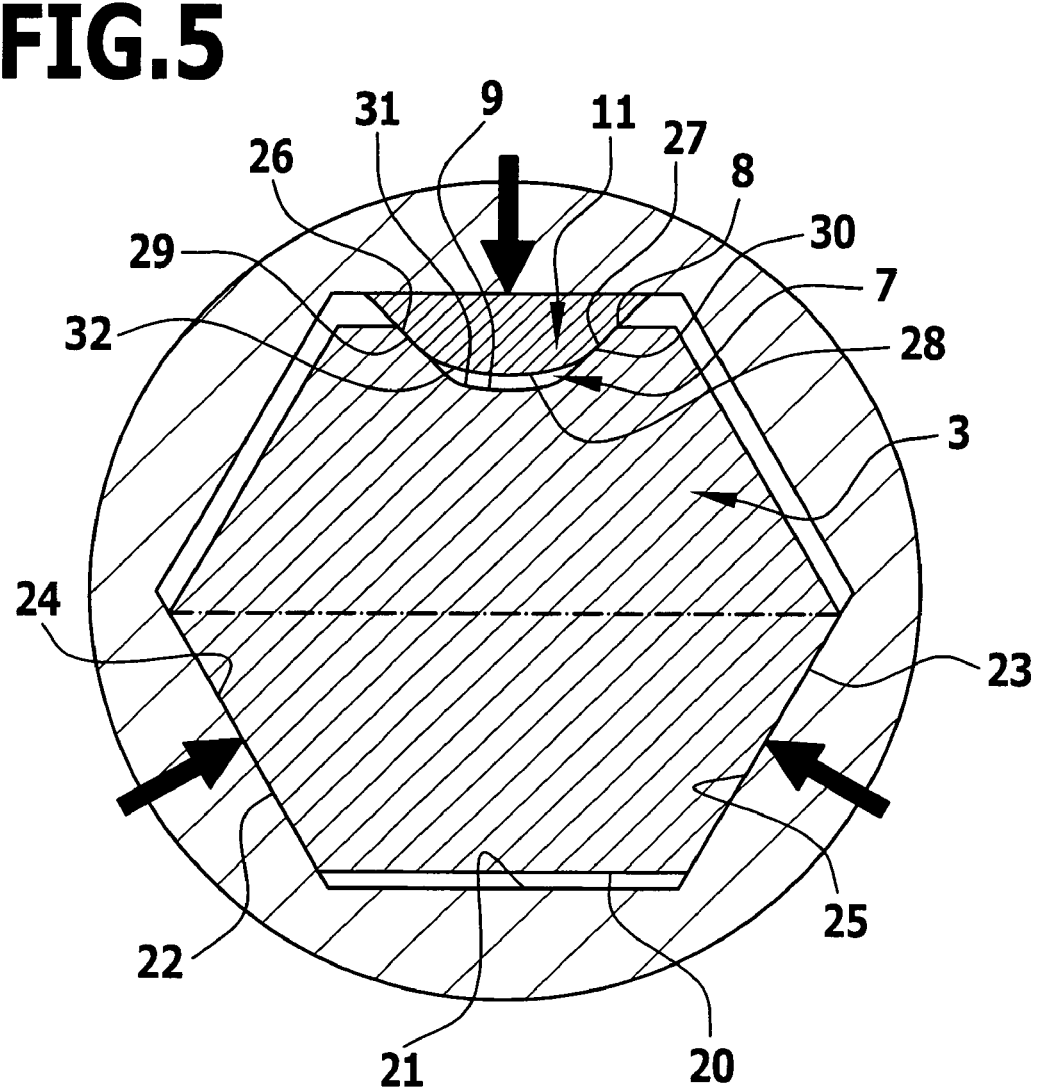
FIG. 5 shows a view similar to FIG. 4 with the longitudinal groove having a rounded-off contour.

The embodiment of FIG. 5 corresponds substantially to that of FIG. 4 and differs from it only in that the side surfaces 26 and 27 do not continue along a sharp edge into the planar bottom 9 of the longitudinal groove 7 but along a rounding-off 31. In addition, the bottom 9 is not of planar configuration, but is arcuate in cross section. Similarly, provision is made in the bar 11 for the side surfaces 29 and 30 to continue via a rounding-off 32 into the underside 28, and the underside 28 is likewise not of planar, but of arcuate cross section. Sharp edges are avoided by this configuration, and, as a result, the stability of the shaft 3 is further optimized in this area. In this case, too, a mounting of the bar 11 without play in the longitudinal groove 7 is ensured.

Figure 6:
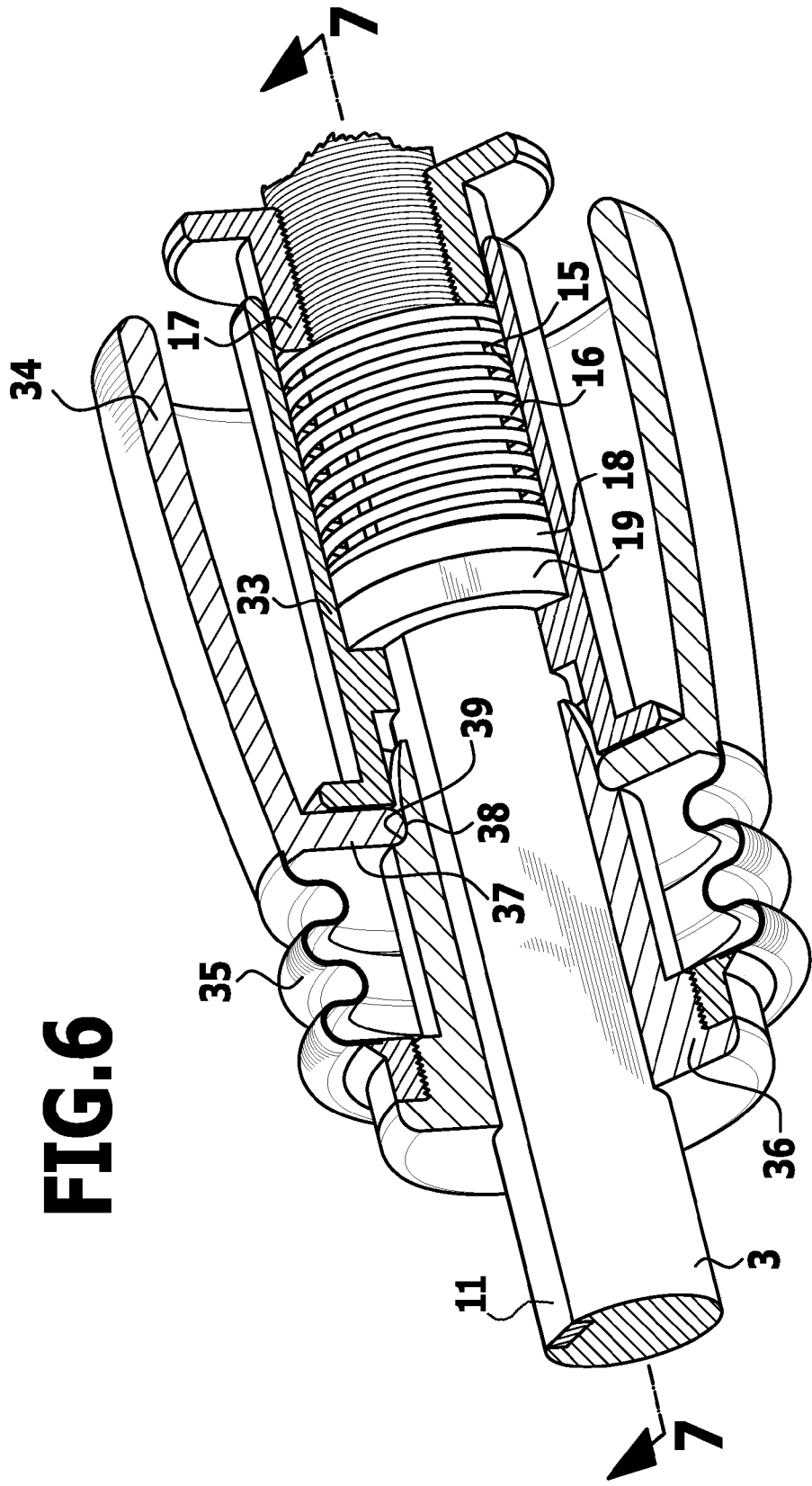
FIG. 6 shows a perspective sectional view of a further embodiment of a screwdriver in the area of the advancing device with an actuating element in the form of a swivel sleeve with a relaxed spring element.

Whereas in the embodiment of FIGS. 1 and 2, the bar 11 can be displaced by grip sleeve 13 against the action of the helical spring 16, in the modified embodiment of FIGS. 6 and 7 a sleeve 33 corresponding to the grip sleeve 13 is provided, but this cannot be directly displaced by the user via gripping surfaces against the action of the helical spring 16, but by a swivel sleeve 34 that surrounds the sleeve 33. The swivel sleeve 34 surrounds the sleeve 33 in spaced relation thereto, and at its distal end, it is connected via an elastically deformable bellows 35, concentrically surrounding the shaft 3, to a supporting ring 36, which concentrically surrounds the shaft 3 and is fixedly connected thereto.

The swivel sleeve 34 carries at the proximal end of the bellows 35 and hence at its distal end a radially inwardly projecting ring flange 37 whose inner edge 38 is supported on a ring shoulder 39 of the supporting ring 36. This supporting of the ring flange 37 on the ring shoulder 39 forms a pivot bearing point for the swivel sleeve 34. When the swivel sleeve 34 is pressed at a point on its circumference against the shaft 3, this results in a swiveling of the swivel sleeve 34 about such a bearing point, which then lies on the opposite side of the user's point of engagement, as shown in FIG. 7. A pressure on the outer rim of the swivel sleeve 34 in the direction of arrow A in FIG. 7 thus causes a swiveling about a swivel point B (FIG. 7) which is fixed on the shaft. The ring flange 37 is thereby moved on a circular path on the side opposite the swivel point B and is lifted off the ring shoulder 39. The circular path is indicated by the radius C in FIG. 7. On the side opposite the swivel point B, this also results in an axial displacement of the ring flange 37, and the ring flange 37 transmits this axial displacement to the sleeve 33 abutting directly thereon. The sleeve 33 is thereby displaced in proximal direction against the action of the helical spring 16, i. e., the ring flange 37 also acts as driver to displace the sleeve 33 and hence to displace the bar 11.

The user can press the swivel sleeve 34 at any point along its circumference against the shaft. A swivel point B is then always formed on the opposite side, and it displaces the ring flange 37 axially and, as a result, the sleeve 33 on the same side as that on which the swivel sleeve 34 is pressed.

In the embodiment shown in FIGS. 6 and 7, the sleeve 33 is pushed back into the initial position again by the helical spring 16, and the swivel sleeve 34 is thereby also swiveled into the initial position again in which it is arranged concentrically with the sleeve 33.

This return movement can be reinforced by the elastic resetting forces of the bellows 35. If the bellows is of suitable configuration, the elastic resetting force of the bellows 35 can also be used on its own to displace the sleeve 33 into the distal end position, but it is then necessary to provide between the sleeve 33 and the ring flange 37 an additional connection, which takes the sleeve 33 along with it when the ring flange is displaced in distal direction. Such a connection is not provided in the embodiment of FIGS. 6 and 7, where the ring flange 37 merely abuts on the sleeve 33 and can displace it upon axial displacement in proximal direction.

The invention claimed is:

1. Screwdriver for bone screws, comprising:
a handle,
a shaft rotationally fixedly held on the handle, a free end of the shaft having a non-circular cross section and being insertable in a positively locked manner in a non-circular receiving opening in a head of a bone screw,
at least one expander element mounted so as to be displaceable in a longitudinal direction in the shaft and so as to slide, when displaced in the longitudinal direction, along a slide surface in an area of the free end of the shaft in such a way that the at least one expander element projects laterally over a contour of the shaft, and
an elastic spring element for pretensioning the at least one expander element in a direction towards the free end of the shaft, the at least one expander element being retractable against action of the spring element in the shaft until the at least one expander element no longer projects laterally over the contour of the shaft,
wherein:
the at least one expander element is connected via a transmission member to an advancing device located on the handle,
the elastic spring element is part of the advancing device;
the advancing device comprises a sleeve which is connected to the at least one expander element and is displaceable on the shaft; and
a swivel element which is mounted on the shaft for swivel movement at one end and is able to swivel about a bearing point against an outer surface of the shaft is provided for displacing the sleeve, and the swivel element comprises a driver which displaces the sleeve against the action of the spring element when the swivel element is swiveled against the shaft.

2. Screwdriver in accordance with claim 1, wherein a stop is provided for limiting movement of the at least one expander element in the direction towards the free end of the shaft.

3. Screwdriver in accordance with claim 1, wherein the transmission member comprises at least one bar which is placed in at least one longitudinal groove which is laterally open and extends over the entire shaft as far as the handle.

4. Screwdriver in accordance with claim 1, wherein the swivel element is configured as a swivel sleeve surrounding the sleeve.

5. Screwdriver in accordance with claim 1, wherein the swivel element is held by an elastically deformable holder on the shaft, and the bearing point is formed by a supporting element of the swivel element on the shaft.

6. Screwdriver in accordance with claim 5, wherein the holder is formed by a bellows concentrically surrounding the shaft.

7. Screwdriver in accordance with claim 5, wherein the supporting element is formed by a ring flange projecting inwardly on an inner side of the swivel sleeve.

8. Screwdriver in accordance with claim 7, wherein the ring flange forms the driver.

9. Screwdriver in accordance with claim 6, wherein the spring element is formed by the bellows.

10. Screwdriver in accordance with claim 1, wherein the sleeve surrounds the shaft in spaced relation thereto, and a helical spring which surrounds the shaft and is supported on the shaft and on the at least one expander element is arranged as the spring element in a ring space between sleeve and shaft.

11. Screwdriver in accordance with claim 3, wherein the at least one longitudinal groove and the at least one bar are of such dimensions that, at least in the area of the free end of the shaft, the at least one bar engages the at least one longitudinal groove without play.

12. Screwdriver in accordance with claim 11, wherein the at least one longitudinal groove and the at least one bar have, at least in the area of the free end of the shaft, planar side surfaces having an identical inclination and converging towards a bottom of the at least one groove.

13. Screwdriver in accordance with claim 12, wherein the at least one bar is, at least in the area of the free end of the shaft, wider on an underside of the at least one bar facing the bottom of the at least one groove than the bottom of the at least one groove, so that a spacing remains between the underside and the bottom of the groove when inserting the at least one bar into the at least one longitudinal groove.

14. Screwdriver in accordance with claim 12, wherein side walls of the at least one longitudinal groove continue, at least in the area of the free end of the shaft, via a rounding-off, into the bottom of the groove.

15. Screwdriver in accordance with claim 14, wherein the bottom of the groove has, at least in the area of the free end of the shaft, an arcuate cross section.

16. Screwdriver in accordance with claim 14, wherein side walls of the at least one bar continue, at least in the area of the free end of the shaft, via a rounding-off into an underside of the at least one bar.

17. Screwdriver in accordance with claim 15, wherein an underside of the at least one bar has, at least in the area of the free end of the shaft, an arcuate cross section.

18. Screwdriver in accordance with claim 1, wherein the non-circular receiving opening and the non-circular cross section of the free end of the shaft are configured such that the shaft is pressed by the expander element in two areas of the receiving opening that are separate from one another against an inside wall of the receiving opening.

19. Screwdriver in accordance with claim 18, wherein:
the receiving opening has a shape of a regular symmetrical hexagon or octagon,
the shaft is of a substantially complementary shape, and
a side surface of the shaft that lies opposite the at least one expander element is set back radially inwardly to a slight extent.

* * * * *